US00PP08199P

United States Patent [19]

Moore

[11] Patent Number: Plant 8,199

[45] Date of Patent: Apr. 13, 1993

[54] HYBRID RUGOSA ROSE PLANT NAMED 'MORTEN'

[75] Inventor: Ralph S. Moore, Visalia, Calif.

[73] Assignee: Sequoia Nursery, Visalia, Calif.

[21] Appl. No.: 784,270

[22] Filed: Oct. 29, 1991

[51] Int. Cl.[5] ..... A01H 5/00

[52] U.S. Cl. ..... Plt./1

[58] Field of Search ..... Plt. 1, 28, 29, 6

*Primary Examiner*—Howard J. Locker

[57] ABSTRACT

This invention relates to a new and distinct variety of shrub type rose plant primarily identified by the vigorous plant and the abundance of red buds and flowers.

1 Drawing Sheet

1

The present invention relates to a new and distinct variety of hardy, shrub type rose plant of the Hybrid Rugosa class; the variety being primarily characterized — as to novelty — by the rich red buds and flowers and the vigorous healthy plant.

The variety is further characterized by:

An abundance of bloom, with flowers usually borne in clusters of 5 to 25 or more.

Little or no fragrance.

A plant which is vigorous, of rounded, upright shape with large size, semi-glossy rugose foliage with pointed leaflets; the buds and flowers being similar in form and size to Paul's Scarlet (climber) (not patented).

The plant, which has a normal height of 5-6 feet or more, can easily be maintained at lesser height by occasional trimming.

A plant which grows and blooms satisfactorily outdoors; is good for growing in large pots, but best as a flowering shrub, in mass landscape planting and as a flowering hedge.

The present variety of hybrid rugosa was originated by me at my nursey located at Visalia, Calif., under conditions of careful control and observation, as a cross between Anytime (miniature, not patented) as the seed parent and Rugosa Magnifica (Rugosa — not patented) as the pollen parent.

Subsequent to origination of the variety I successfully asexually reproduced it at the some nursey, located as aforesaid, by budding as well as by cuttings; the reproductions having run true in all respects.

The color photographs illustrate the variety, including the foliage, buds and flowers. The upper photograph illustrates a whole plant view, and the lower photograph a closeup view of a typical blooming cluster.

Referring now specifically to the new and distinct variety of shrub rose plant, the following is a detailed description thereof in outline; all major color plate identifications being by reference to The British Colour Council Horticultural Colour Chart, except where common terms of color definition are employed.

Type: Hardy; vigorous; bushy; upright; seedling; outdoors; garden decoration; landscape.

Class: Hybrid Rugosa.

*Variety identification.*—Morten (Commercial synonym: Linda Campbell).

Flowers borne: In sprays or clusters of 5 to 25 or more on stiff wirey stems.

2

Quantity of bloom: Abundant: repeats several times each season.

Bud:

*Sepals.*—Permanent; spear shaped; recurved.

*Peduncle.*—Medium to long; slender but sturdy; erect; medium to light green, sometimes tinted bronze (outdoors); with no prickles and numerous very short hairs (similar to peach fuzz).

*Before calyx breaks.*—Size — medium. Form long; pointed, covered with numerous short hairs or fuzz on surface of bud; with foliaceous parts extending beyond the tip of the bud equal to one-half or more of its length. Color — medium green, occasionally tinted with bronze (outdoors).

*As calyx breaks.*—Color — red, with small white area at base. Opening: opens well in all weather.

Bloom:

*Size when fully open.*—Medium, averaging about 6.5 to 7.5 cm ( 2¾ to 3").

*Petalage.*—Double — averaging about 15-20 petals, arranged regularly, plus several small petaloids.

*Form.*—Open with petals rolled loosely outward and downward. Open flowers show stamens.

Petals: Fairly thick; velvety on inside and satiny on outside surface.

*Shape.*—Outside petals, broad lanceolate with rounded tip; intermediate — broad lanceolate with rounded tip; inside — broad lanceolate with rounded tip.

*Color*—. newly opened flower from a plant grown outdoors (Jul. 1991), Visalia, Calif. Outside petal: Outside surface — near Rose Red 724 (both lighter and darker) with a slight blueish cast (or veining), becoming yellowish to white near base. Inside surface — near Currant Red (with blackish tones or veining), becoming blueish and then whitish to yellowish in small area at base. Intermediate petal: Outside surface similar to outside petal. Inside surface similar to outside petal. Inner petal: Outside surface — same as intermediate petal; inside surface — same as intermediate petal. General color effect; buds and newly opened flowers — bright red similar to Paul's Scarlet with lighter reverse. Note: Color can vary slightly, depending upon weather, time of year, light intensity, etc. Three days open — color — similar to newly opened flowers. Behavior — opens well in all weather. Spent petals drop off. Flower longevity — 6–10 days or longer on plant. Not a cutting flower.

Reproductive Organs:

*Stamens.*—Arranged regularly about pistils.

*Filaments.*—Varying length, short, yellow.

*Anthers.*—Well formed; yellow.

*Pollen.*—some.

*Pistils.*—average number.

*Styles.*—varying length — very short; whitish, bunched.

*Ovaries.*—all enclosed in calyx.

*Hips.*—none.

Seed: none.

Foliage:

*Leaves.*—Compound of seven to nine leaflets; medium to large size; leathery; semi-glossy to matte — often 16–18 cm in length and 6–10 cm wide.

*Leaflets.*—Shape: broad, nearly oval; apex acute; base rounded, edges serrated. Color: medium green; new growth — normal (medium) green (sometimes tinted reddish). Rachis: strong, slender; upper side usually free of prickles; grooved; underside may have several short thorns (1 to 3). Stipules: medium to short length; medium width, with serrated edges; short to medium length, narrow points which turn out usually at about 45 degrees or less.

Growth:

*Habit.*—Vigorous; bushy; upright; much branched.

*Growth.*—Free; vigorous.

*Canes.*—Strong; sturdy.

*Main stems.*—Color: medium green, becoming brownish with age.

*Thorns.*—several, medium to long, usually straight. (Note: This plant is much less thorny than most other varieties in the rugosa class.) Prickles — None. Hairs — none.

*Branches.*—Color: medium green. Thorns: few to several; slender; medium to long — straight. Prickles: none. Hairs — none.

The Hybrid Rugosa (shrub ) rose plant and its flowers as herein described may vary in slight detail due to climatic, soil and cultural conditions under which the variety may be grown; the present description being of the variety as grown at Visalia, Calif.

The following is claimed:

1. A new and distinct variety of Hybrid Rugosa shrub rose plant of hardy, bushy, upright, much branced habit, substantially as illustrated and described, characterized by buds and flowers of decorative (informal) form, essentially medium red in color, with reverse of petals being a slightly lighter shade of red, and further characterized by the plant of vigorous well rounded shape, with the main stems and shoots being moderately thorny, said plant being easy to propagate from cuttings or by budding, with an abundance of medium to large (Rugosa type) semi-glossy to matte foliage and an abundance of flowers borne in sprays or clusters of 5 to 25 or more.

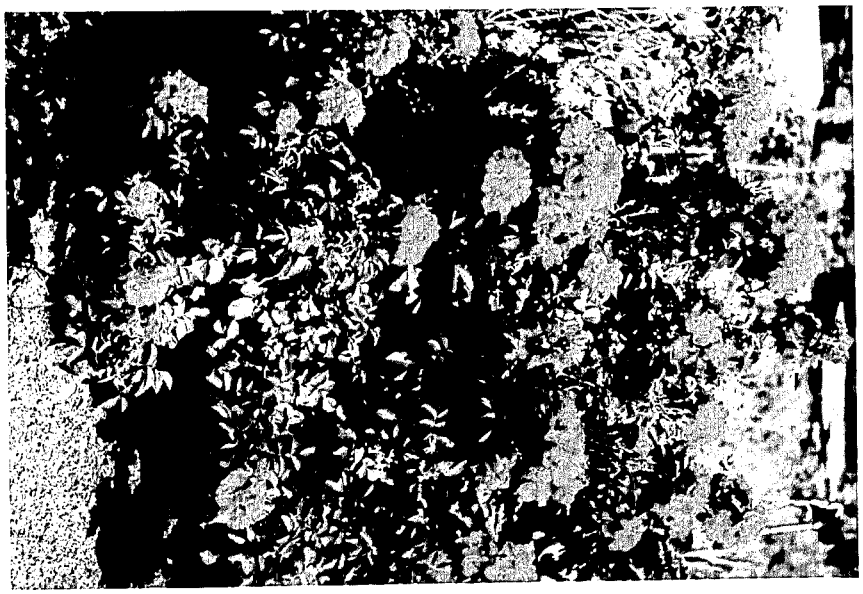
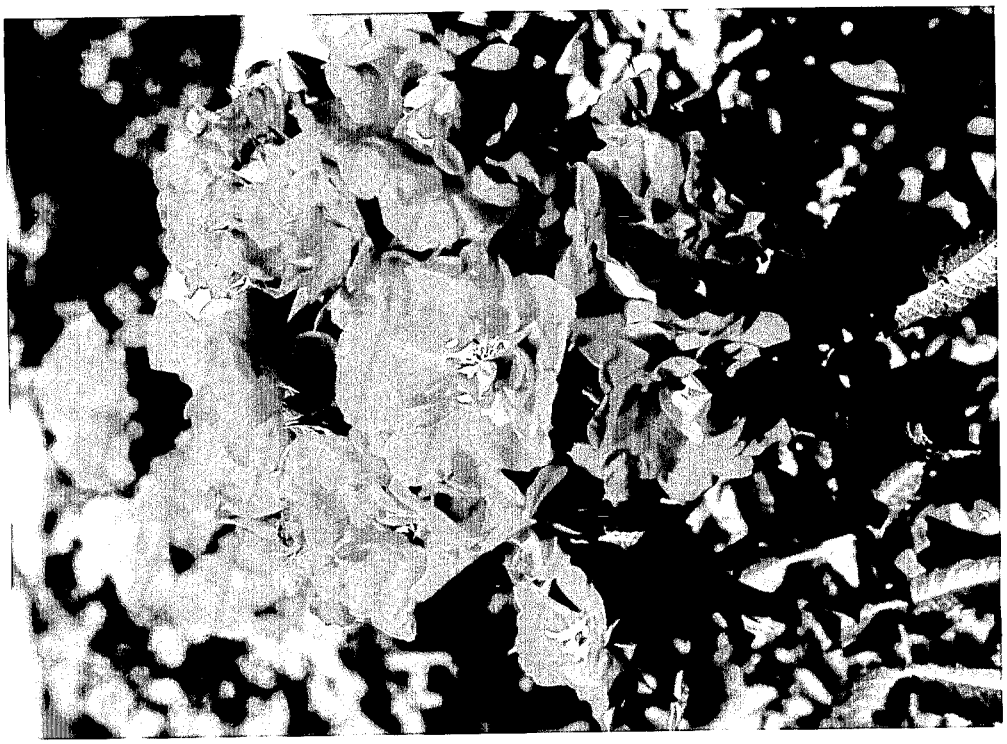

* * * * *